United States Patent [19]

Tsuchiya et al.

[11] 4,216,772
[45] Aug. 12, 1980

[54] ABSORBENT ARTICLE

[75] Inventors: Yoshimi Tsuchiya; Hiroshi Mizutani, both of Yachiyo, Japan

[73] Assignee: Kao Soap Co., Ltd., Tokyo, Japan

[21] Appl. No.: 942,886

[22] Filed: Sep. 15, 1978

[30] Foreign Application Priority Data

Feb. 8, 1978 [JP] Japan .................................. 53-13136

[51] Int. Cl.³ ............................................. A61F 13/16
[52] U.S. Cl. ................................ 128/284; 128/290 W
[58] Field of Search ............................ 128/155–156, 128/284–285, 287, 290 R, 290 W; 428/212–213, 219, 297, 224

[56] References Cited

U.S. PATENT DOCUMENTS

| 2,862,251 | 12/1958 | Kalwaites | 128/290 W |
| 3,695,269 | 10/1972 | Malaney | 128/284 |
| 3,804,092 | 4/1974 | Tunc | 128/284 |
| 4,129,132 | 12/1978 | Butterworth et al. | 128/287 |

Primary Examiner—C. Fred Rosenbaum
Attorney, Agent, or Firm—Blanchard, Flynn, Thiel, Boutell & Tanis

[57] ABSTRACT

A disposable absorbent article in which the surface material is a non-woven fabric comprising from 60 to 90 wt. % of hydrophilic fibers and the balance, i.e., from 40 to 10 wt. %, of the fabric is hydrophobic fibers, and wherein the hydrophilic fibers used therein comprise two kinds of fibers of different thicknesses, i.e., from 10 to 90 wt. % of hydrophilic fibers having a thickness of from 1.5 to 3 denier and the balance of from 90 to 10 wt. % of hydrophilic fibers having a thickness of from 4 to 7 denier.

6 Claims, 2 Drawing Figures

ABSORBENT ARTICLE

BACKGROUND OF THE INVENTION

1. Field of the Invention

The present invention relates to a disposable absorbent article, particularly a disposable absorbent article such as a menstruation napkin or a disposable diaper. More particularly, the present invention relates to a disposable absorbent article, such as a menstruation napkin or a disposable diaper, in which the outer surface layer is a non-woven fabric.

2. Description of the Prior Art

Conventional absorbent articles have the disadvantage that even though they absorb fluids eliminated from the body, a part of the body fluids absorbed therein is thereafter pressed out or exuded from the absorbent material through the surface layer thereof, caused by the body weight of the user, so as to wet the skin of the user, thereby making the user uncomfortable or causing skin irritation. In order to minimize the pressing-out of the absorbed body fluids, there has been proposed an improvement wherein a water-repellent non-woven fabric is used as the surface layer of the absorbent article. A hydrophobic substance is used as the binder for the non-woven material or hydrophobic synthetic fibers are used as a part of the fibers of the non-woven fabric. Although the pressing-out of the absorbed body fluids is considerably minimized by this technique, the rate of absorption of the body fluids into the absorbent article is reduced greatly, owing to the water-repellency of the hydrophobic substance or fibers, which causes the fluids to leak from the sides thereof.

SUMMARY OF THE INVENTION

After intensive investigations on (1) the rate of absorption of body fluids into the absorbent article, and (2) the pressing-out of the absorbed body fluids from the absorbent article, which properties counteract each other, we have discovered that a satisfactory absorbent article can be obtained by using, as a surface or covering layer on the absorbent article, a non-woven fabric having a fibrous composition comprising 60 to 90 wt. % of hydrophilic fibers and 40 to 10 wt. % of hydrophobic fibers, and wherein said hydrophilic fibers comprise a mixture of two kinds of fibers, i.e., from 10 to 90 wt. % of relatively thin fibers having a thickness of from 1.5 to 3 denier and from 90 to 10 wt. % of relatively thick fibers having a thickness of from 4 to 7 denier. The present invention has been accomplished on the basis of this finding.

Fibers having a thickness of from 1.5 to 3 denier have mainly been used to make the non-woven fabrics used as the surface layers of absorbent articles. It has not been expected that an excellent absorbent article, as that of the present invention, can be obtained by using thick fibers having a thickness of more than 4 denier as a part of the fibers of the non-woven fabric.

As the hydrophilic fibers usable in the present invention, there can be mentioned cellulose fibers such as cotton and viscose rayon and vinylon fibers. As the hydrophobic fibers, there can be mentioned polyester fibers, polyolefin fibers and polyolefin conjugate fibers.

Although only one kind of hydrophobic fibers can be used, it is preferred to use a suitable mixture of two or more different hydrophobic fibers, particularly in the case of non-woven fabrics prepared by, for example, the heat-fusion adhesion method.

The non-woven fabric used as the surface layer of the absorbent article preferably has a weight of 15 to 30 g/m$^2$. If the relatively thin hydrophilic fibers are contained in an amount higher than 90 wt. %, based on the total amount of the hydrophilic fibers, the thickness of the non-woven fabric layer will be too high and, on the other hand, if the amount of the relatively thick hydrophilic fibers is higher than 90 wt. %, based on the total amount of the hydrophilic fibers, the thickness of the non-woven fabric layer will be too low.

The following examples further illustrate the present invention.

EXAMPLE 1

Figure 1:
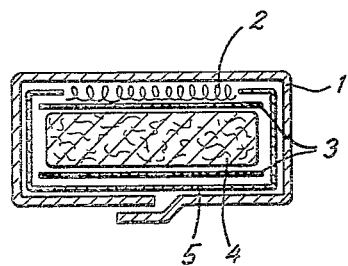
FIG. 1 is a sectional view of the menstruation napkin described in Example 1.

There were prepared menstruation napkins of a size of 70–190 mm and comprising a non-woven fabric 1, a rayon staple layer 2 (0.4 g), an absorbent tissue 3 (0.6 g), a fluffed pulp 4 (4.0 g) and a water-repellent tissue 5 (0.6 g), as shown in FIG. 1. Using various non-woven fabrics set forth in Table 1 as the non-woven fabric, the absorption rate and the amount of absorbed body fluids pressed out were measured. The results are shown in Table 1.

The absorption rate and the pressed-out fluid (hereinafter called "wet-back") were measured by the following methods:

Absorption rate: A fibrinogen-free horse blood was deposited dropwise on the upper surface of an inclined sample napkin and the flow of the blood was observed. The length of the flow path along the napkin before the horse blood was fully absorbed therein was determined. The shorter the length, the higher is the absorption rate.

Wet back: A given quantity of the fibrinogen-free horse blood was allowed to be absorbed by a sample napkin. After a given period of time, the sample napkin was pressed and the quantity of the blood that was pressed out was measured.

Table 1

| Sample No. | Hydrophilic fibers *1 Thin fibers Type | Amount | Thick fibers Type | Amount | Hydrophobic fibers *2 Type | Amount | Weight of non-woven fabric 1 | Absorption rate | Wet Back | Remarks |
|---|---|---|---|---|---|---|---|---|---|---|
| 1 | R1.5d | 20% | | 0 | ES | 80% | 21g/m$^2$ | 150 mm | 4.2 g | Conventional |
| 2 | R1.5d | 60 | | 0 | ES | 40 | 21 | 55 | 4.5 | Napkin |
| 3 | R1.5d | 90 | | 0 | ES | 10 | 19 | 20 | 6.3 | Ordinary |
| 4 | R3.0d | 40 | | 0 | ES | 60 | 20 | 150 | 3.9 | |
| 5 | R3.0d | 80 | | 0 | ES | 20 | 17 | 30 | 6.1 | |
| 6 | R1.5d | 10 | R5d | 10% | ES | 80 | 18 | 150 | 4.2 | Comparison |

Table 1-continued

| Sample No. | Hydrophilic fibers *1 | | | | Hydrophobic fibers *2 | | Weight of non-woven fabric 1 | Absorption rate | Wet Back | Remarks |
|---|---|---|---|---|---|---|---|---|---|---|
| | Thin fibers | | Thick fibers | | | | | | | |
| | Type | Amount | Type | Amount | Type | Amount | | | | |
| 7 | R1.5d | 20 | R7d | 20 | ES | 60 | 20 | 130 | 4.8 | |
| 8 | R1.5d | 20 | R5d | 40 | ES | 40 | 23 | 30 | 3.2 | |
| 9 | R1.5d | 30 | R7d | 30 | ES | 40 | 18 | 30 | 3.1 | |
| 10 | R3.0d | 40 | R5d | 20 | ES | 40 | 18 | 25 | 3.4 | |
| 11 | R1.5d | 20 | R5d | 60 | ES | 20 | 21 | 20 | 2.9 | Present invention |
| 12 | R3.0d | 40 | R7d | 40 | ES | 20 | 17 | 25 | 3.1 | |
| 13 | R3.0d | 60 | R5d | 20 | ES | 20 | 19 | 15 | 3.0 | |
| 14 | R1.5d | 40 | R7d | 50 | ES | 10 | 18 | 10 | 3.2 | |
| 15 | R1.5d | 70 | R7d | 20 | ES | 10 | 20 | 10 | 3.3 | |
| 16 | R3d | 60 | | 0 | ES PET | 20% 20 | 20 g/m² | 25 mm | 4.1 | Comparison |
| 17 | R3d | 30 | R5d | 30% | ES PET | 20 20 | 21 | 20 | 3.2 | Present invention |
| 18 | R1.5d | 10 | R5d | 10 | ES PET | 40 40 | 18 | 150 | 3.5 | Comparison |
| 19 | | 0 | | 0 | PP | 100 | 17 | 150 | 4.5 | |
| 20 | | 0 | | 0 | PP | 100 | 23 | 150 | 3.6 | |
| 21 | B1.5d | 40 | B5d | 30 | ES | 30 | 17 | 25 | 3.4 | Present invention A little rigid |
| 22 | B3d | 20 | B5d | 10 | ES | 70 | 18 | 150 | 3.8 | Comparison A little rigid |

The symbol "d" means denier
*1 R; Rayon B; Vinylon
*2 ES; Polyolefin conjugate fibers (3 d) PP; Polypropylene fibers (3 d) PET; Polyester fibers (2 d)
(The above symbols have the same meanings in the following examples).

EXAMPLE 2

Figure 2:
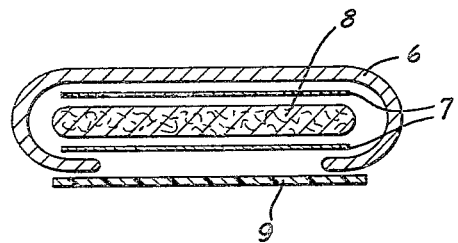
FIG. 2 is a sectional view of the disposable diaper described in Example 2.

There were prepared disposable diapers of a size of 400×250 mm comprising a non-woven fabric 6, absorbent tissue 7 (1 g×2), a pulp fluff 8 (25 g) and a polyethylene sheet 9 (5.5 g) as shown in FIG. 2. Using various non-woven fabrics as described in Table 2, the absorption rate and wet back were examined. The results are shown in Table 2. The methods of measurement were the same as in Example 1, except that urine was used in place of the fibrinogen-free horse blood used in Example 1 and the quantity of the non-absorbed urine flowing off from the sample diaper (without being absorbed) was measured in the determination of the absorption rate.

Table 2

| Sample No. | Hydrophilic fibers *1 | | | | Hydrophobic fibers *2 | | Weight of non-woven fabric 1 | Absorption rate | Wet Back | Remarks |
|---|---|---|---|---|---|---|---|---|---|---|
| | Thin fibers | | Thick fibers | | | | | | | |
| | Type | Amount | Type | Amount | Type | Amount | | | | |
| 1 | R1.5d | 20% | | 0 | ES | 80% | 21 g/m² | 14.2 g | 10.1 g | Comparison |
| 2 | R3d | 60 | | 0 | ES | 40 | 21 | 3.1 | 22.3 | |
| 3 | R1.5d | 90 | | 0 | ES | 10 | 19 | 1.5 | 24.5 | |
| 4 | R1.5d | 20 | R5d | 40% | ES | 40 | 23 | 1.8 | 8.2 | Present invention |
| 5 | R3d | 40 | R7d | 40 | ES | 20 | 17 | 0.5 | 10.0 | |
| 6 | R1.5d | 10 | R5d | 10 | ES | 80 | 18 | 13.1 | 9.3 | Comparison |
| 7 | R3d | 30 | R5d | 30 | ES PET | 20 20 | 21 | 2.5 | 11.4 | Present invention |
| 8 | R1.5d | 10 | R5d | 10 | ES PET | 40 40 | 20 | 16.3 | 10.6 | Comparison |
| 9 | | 0 | | 0 | PP | 100 | 23 | 16.8 | 7.2 | |

EXAMPLE 3

Commercially available menstruation napkins A, B and C were compared with a product of the present invention with respect to absorption rate and wet back in the same manner as described in Example 1. The results shown in Table 3 were obtained. The non-woven fabric used in the product of the present invention had the following composition:
Rayon: 1.5 d, 20%
Rayon: 5 d, 60%
Polyolefin conjugate fibers: 3 d, 20%
Weight of fabric: 21 g/m²

Table 3

| Sample | Non-woven fabric | Weight g/m² | Absorption mm | Wet Back g | Remarks (weight of sample) |
| --- | --- | --- | --- | --- | --- |
| A | Mainly composed of rayon (Wet) Binder type | 20 | 150 | 4.5 | 6.4 g |
| B | Mainly composed of rayon (Dry) Binder type | 18 | 95 | 3.8 | 7.2 |
| C | Mainly composed of rayon (Dry) PP - Binder type | 20 | 53 | 3.6 | 6.8 |
| Present Invention | | 21 | 20 | 3.0 | 6.2 |

EXAMPLE 4

Commercially available disposable diapers D, E and F were compared with a product of the present invention with respect to absorption rate and wet back in the same manner as described in Example 2. The results shown in Table 4 were obtained. The non-woven fabric used in the product of the present invention had the following composition:

Rayon: 1.5 d, 20%
Rayon: 5 d, 40%
Polyolefin conjugate fibers: 3 d, 40%
Basis weight: 23 g/m²

Table 4

| Sample | Non-woven fabric | Basis weight g/m² | Absorption rate g | Wet Back g |
| --- | --- | --- | --- | --- |
| D | Mainly composed of rayon (Wet) | 23 | 2.1 | 23.4 |
| E | Mainly composed of rayon (Dry) | 30 | 4.2 | 16.2 |
| F | Mainly composed of polyester | 21 | 11.4 | 9.6 |
| Present Invention | | 23 | 1.5 | 8.3 |

The enbodiments of the invention in which an exclusive property or privilege is claimed are defined as follows:

1. In an absorbent article for absorbing body fluids and exudations comprising an absorbent core which is partially or completely enveloped by a surface cover layer, wherein said surface cover layer is a non-woven fabric having a weight of about 15 to 30 g/m² and is made of a fibrous composition consisting essentially of about 60 to 90 wt. % of hydrophilic fibers and about 40 to 10 wt. % of hydrophilic fibers, the improvement which comprises: said hydrophilic fibers consist essentially of from about 10 to 90 wt. % of hydrophilic fibers having a thickness of about 1.5 to 3 denier and from about 90 to 10 wt. % of hydrophilic fibers having a thickness of about 4 to 7 denier.

2. An absorbent article according to claim 1 wherein one side of said core has a fluid impervious barrier sheet in association therewith to prevent passage of body fluids and exudates outwardly from one side of said absorbent article.

3. An absorbent article as claimed in claim 1 which is a disposable sanitary napkin.

4. An absorbent article as claimed in claim 1 which is a disposable diaper.

5. An absorbent article according to claim 1 in which said absorbent core comprises cellulosic fibers.

6. An absorbent article according to claim 1 in which said hydrophilic fibers are selected from the group consisting of cotton fibers, viscose rayon fibers, vinylon fibers and mixtures thereof, and said hydrophobic fibers are selected from the group consisting of polyester fibers, polyolefin fibers, polyolefin conjugate fibers and mixtures thereof.

* * * * *

UNITED STATES PATENT OFFICE
CERTIFICATE OF CORRECTION

Patent No. 4 216 772          Dated August 12, 1980

Inventor(s) Yoshimi Tsuchiya et al

It is certified that error appears in the above-identified patent and that said Letters Patent are hereby corrected as shown below:

Column 6, Line 24; change "hydrophilic" to ---hydrophobic---.

Signed and Sealed this

Eleventh Day of November 1980

[SEAL]

Attest:

SIDNEY A. DIAMOND

Attesting Officer

Commissioner of Patents and Trademarks